(12) United States Patent
Agache et al.

(10) Patent No.: US 12,179,198 B2
(45) Date of Patent: Dec. 31, 2024

(54) MICROFLUIDIC SYSTEM FOR HANDLING BIOLOGICAL CELLS

(71) Applicant: COMMISSARIAT A L'ENERGIE ATOMIQUE ET AUX ENERGIES ALTERNATIVES, Paris (FR)

(72) Inventors: Vincent Agache, Monestier de Clermont (FR); Fabrice Casset, Tencin (FR); Stephane Fanget, Le Grand Lemps (FR); Yves Fouillet, Voreppe (FR); Arnaud Millet, Voreppe (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 1293 days.

(21) Appl. No.: 16/475,901

(22) PCT Filed: Jan. 5, 2018

(86) PCT No.: PCT/FR2018/050022
§ 371 (c)(1),
(2) Date: Jul. 3, 2019

(87) PCT Pub. No.: WO2018/127666
PCT Pub. Date: Jul. 12, 2018

(65) Prior Publication Data
US 2019/0344278 A1    Nov. 14, 2019

(30) Foreign Application Priority Data

Jan. 6, 2017 (FR) ...................................... 17 50134

(51) Int. Cl.
*C12Q 1/04* (2006.01)
*B01L 3/00* (2006.01)
(Continued)

(52) U.S. Cl.
CPC .......... *B01L 3/502761* (2013.01); *C12Q 1/04* (2013.01); *G01N 15/10* (2013.01);
(Continued)

(58) Field of Classification Search
None
See application file for complete search history.

(56) References Cited

U.S. PATENT DOCUMENTS

| 2005/0014162 | A1  | 1/2005 | Barth |              |
|--------------|-----|--------|-------|--------------|
| 2006/0046305 | A1* | 3/2006 | Liu   | B82Y 5/00    |
|              |     |        |       | 436/164      |

(Continued)

OTHER PUBLICATIONS

U.S. Appl. No. 14/114,009, filed Oct. 25, 2013, US No. 2014/0044568, Fouillet, Y. et al.
(Continued)

*Primary Examiner* — Matthew D Krcha
*Assistant Examiner* — Brittany I Fisher
(74) *Attorney, Agent, or Firm* — Oblon, McClelland, Maier & Neustadt, L.L.P.

(57) ABSTRACT

A system for handling biological cells includes a main channel having an inlet end and an outlet end, and, at least over a first portion from the inlet end, including a cross section such that a cell circulating in the portion undergoes mechanical stresses. The system further includes first means for detecting the presence of a cell at the inlet end of the main channel and at least one access zone opening into the main channel between its inlet end and its outlet end in the first portion, in order to make it possible to exert an action on the cell. The system also includes means for displacing the cell in order to control the displacement of the cell between the inlet end and the outlet end.

17 Claims, 5 Drawing Sheets

(51) Int. Cl.
*C12M 1/26* (2006.01)
*G01N 15/01* (2024.01)
*G01N 15/10* (2024.01)

(52) U.S. Cl.
CPC ............... *B01L 2200/0647* (2013.01); *B01L 2300/0645* (2013.01); *G01N 15/01* (2024.01); *G01N 2015/1021* (2024.01)

(56) References Cited

U.S. PATENT DOCUMENTS

| | | | |
|---|---|---|---|
| 2007/0072290 A1 | 3/2007 | Hvichia | |
| 2009/0098541 A1* | 4/2009 | Southern | B01L 3/502753 435/287.1 |
| 2011/0045994 A1* | 2/2011 | Voldman | G01N 33/5005 506/10 |
| 2012/0052567 A1 | 3/2012 | Hvichia | |
| 2012/0148140 A1* | 6/2012 | Di Carlo | G01N 1/31 382/133 |
| 2012/0225418 A1* | 9/2012 | Meyer | G01N 15/1459 210/96.1 |
| 2014/0072952 A1 | 3/2014 | Hvichia | |
| 2014/0072953 A1 | 3/2014 | Hvichia | |
| 2016/0340636 A1* | 11/2016 | Tabata | G01N 15/147 |
| 2016/0340644 A9 | 11/2016 | Hvichia | |

OTHER PUBLICATIONS

U.S. Appl. No. 15/046,803, filed Feb. 18, 2016, US No. 2016/0244715, Casset, F. et al.
U.S. Appl. No. 15/335,702, filed Oct. 27, 2016, US No. 2017/0121661, Casset, F. et al.
U.S. Appl. No. 16/244,257, filed Jan. 10, 2019, Casset, F. et al.
U.S. Appl. No. 16/335,511, filed Mar. 21, 2019, Casset, F. et al.
International Search Report issued on Apr. 20, 2018, in PCT/FR2018/050022 filed on Jan. 5, 2018.
Preliminary French Search Report issued on Sep. 21, 2017, in French Patent Application No. 17 50134 filed on Jan. 6, 2017.
Zhang, K. et al., "A microfluidic system with surface modified piezoelectric sensor for trapping and detection of cancer cells", Biosensors And Bioelectronics, vol. 26, No. 2, 2010, pp. 935-939, XP027320417.
Sharei, A. et al., "A vector-free microfluidic platform for intracellular delivery", Proceedings of the National Academy of Sciences (PNAS), vol. 110, No. 6, Feb. 5, 2013, pp. 2082-2087, XP055182922.
Byun, S. et al., "Characterizing deformability and surface friction of cancer cells", Proceedings of the National Academy of Sciences (PNAS), 2013, URL: www.pnas.org/cgi/content/short/1218806110; total 15 pages.
Sheridan, C., "Exosome cancer diagnostic reaches market", Nature Biotechnology, vol. 34, No. 4, Apr. 2016, pp. 359-360.

* cited by examiner

MICROFLUIDIC SYSTEM FOR HANDLING BIOLOGICAL CELLS

TECHNICAL FIELD AND PRIOR ART

This invention relates to a microfluidic system for handling biological cells, in particular for the purpose of treating them and/or analysing them.

In the field of biomedicine, it is sought to be able to analyse and process biological cells individually. For example, circulating tumour cells (CTC) are tumour cells that leave the original tumour and circulate in the organism before installing themselves in a new organ in order to from metastases. Detecting and treating these cells is a substantial challenge. As these cellules are not very numerous, it is also sought to be able to treat them individually and to be able to quickly evaluate the effect of the treatment on the latter.

The document Sangwon Byuna, Sungmin Sonb, Dario Amodeic, Nathan Cermakd, Josephine Shawa, Joon Ho Kange, Vivian C. Hechta, Monte M. Winslowf, g, Tyler Jacksf, h, Parag Mallickc, and Scott R. Manalis. *Characterizing deformability and surface friction of cancer cells Proceedings of the National Academy of Sciences* 110(19), April 2013, describes a device comprising a suspended microchannel resonator (SMR) that allows for an individual counting and weighing of the cells. The resonator comprises a microchannel provided with a portion of reduced section. On the one hand the presence of a cell in the microchannel causes a modification in the resonance frequency of the resonator, which makes it possible to detect the presence of a cell, to count the cells and to obtain certain pieces of information on the cell such as its floating mass, its density. On the other hand, the time taken by the cell to travel the restriction provides other information on the cell, in particular in line with its mechanical properties, here its deformability. This information makes it possible to study the nature of the cell, and to deduce therefrom their metastatic potential when it is a tumour cell.

However the capacity of this device is limited and the device does not make it possible to act on the cell.

The document A. Sharei et al. "*A vector free microfluidic platform for intracellular delivery*", PNAS, Feb. 5, 2013, Vol. 110, no. 6. describes a device for cellular delivery or for transfection comprising several channels, with each one comprising a zone with a reduced section, in order to constrain the cells, transient pores can then by formed, which allows for the transfection in the cells of macromolecules. The cells to be treated and the macromolecules that are to be transfected in the cells are introduced at one end of the channels, they circulate together in the channels. When the cells penetrate into the restriction they are constrained mechanically, which causes pores to appear through which the macromolecules can enter into the cells.

This device has for disadvantage to not allow for a targeted action on the cells. On the one hand there is no way to detect the presence of a cell and therefore to decide to undertake an action or not. On the other hand, it is not possible to carry out a selective action of the cell, indeed all of the cells are transfected. In addition this device only allows for transfection and no other action.

DISCLOSURE OF THE INVENTION

It is consequently a purpose of this invention to offer a microfluidic system for handling biological cells that allows for a targeted, individual and suitable action on the cells, and which also offers great modularity in the actions that can be carried out on the cells.

The purpose announced hereinabove is achieved by a microfluidic system that comprises at least one channel intended to circulate at least one cell to be manipulated, means for detecting the presence of the cell, a zone with a reduced section less than that of the cell and also an access zone to the cell located in the zone of reduced section in order to make it possible to undertake actions on the cell or with regards to the cell.

The information collected by the means for detecting and optionally the time taken by the cell to cross at least one portion of this zone with a reduced section makes it possible to identify the cell.

Thus the actions taken on the cells are taken when a cell is detected and identified. Thus the actions are targeted and useful because they take place only in the presence of cells, in particular of the cells concerned.

Furthermore, the operation of the system according to the invention can be automated by means of a control unit that generates orders to apply an action when a cell is detected and according to the cell detected. The output of the system can therefore be improved.

The combination of the means for detecting, of the channel with a reduced section and of the access zone makes it possible to have a system for handling that is optimised both in terms of function and in size. Indeed the channel with a reduced section participates both in the detection/identification of the cell and in the action on the cell for the transfection and the collection of substance.

Advantageously, second means for detecting downstream of the access zone make it possible to characterise the effect of the action applied on the cell in the access zone, for example by comparing the signals of the first means for detecting and the signals of the second means for detecting.

Advantageously, the first and/or the second means for detecting comprise a vibrating support. The characteristics of the vibration wave of the surface are modified by the arrival of the cell and depend on the size of the cell and on its mechanical properties. These means make it possible to both detect the presence of a cellule but also to identify it at least partially.

The treatment zone can for example allow for the delivery of macromolecules to the cells or the collection of substances ejected by the cells.

Advantageously, an imaging system is provided for example on the access zone.

A subject-matter of the invention then is a system for handling biological cells comprising:
  n main channels, n being a whole number at least equal to 1, with each main channel comprising an inlet end and an outlet end, at least on a first portion starting from its end inlet, a transverse section such as a cell circulating in said portion undergoes mechanical stresses,
  first means for detecting the presence of a cell on the inlet end of the main channel,
  at least one access zone opening into the main channel between its inlet end and its outlet end in said first portion, in order to make it possible to exert an action on the cell,
  means for displacing the cell for controlling the displacement of the cell between the inlet end and the outlet end.

The first means for detecting are advantageously able to provide information on at least one property of the cell.

The first means for detecting can comprise a support forming a portion of the wall of the main channel and at least one actuator able to put into vibration said support.

The system for handling biological cells can also comprise second means for detecting between the access zone and the outlet end.

For example, the access zone comprises a secondary channel and means able to authorise and to interrupt a fluidic communication between the secondary channel and the main channel. The means able to authorise and to interrupt a fluidic communication between the secondary channel and the main channel can comprise a closing element and are such that the closing element is subjected in the secondary channel to two pressures being exerted in the opposite direction, said means controlling said pressures in order to displace the closing element.

The closing element is more preferably a fluid that is immiscible with at least the liquid containing the cell.

In an embodiment, the secondary channel can be intended to be supplied with one or substances to be delivered to the cell.

In another embodiment, the secondary channel is intended to be connected to a zone for collecting one or several substances ejected by the cell. The secondary channel can be intended to be connected to means for analysing the substance or substances ejected by the cell.

Advantageously, at least one portion of a side wall of the main channel is transparent, with the system comprising an imaging system arranged on said transparent portion Preferably, the system for handling comprises a control unit connected at least to the first means for detecting, to the access zone and to the means for controlling the displacement of the cell and able to act at least on the access zone and/or on the means for controlling the displacement of the cell in order to apply an action to the cell Advantageously, the system comprises at least two channels.

The actuator can be a piezoelectric actuator.

Another subject-matter of the invention is a method for handling that implements a system for handling biological cells according to the invention comprising:
a) the supplying of a solution that contains at least one cell at the inlet end of the main channel,
b) displacing of the cell in the main channel,
c) detecting the presence of the cell at the inlet of the main channel,
d) determining at least one property of the cell and optionally the determining of said cell,
e) decision to apply or not an action to the cell,
f) if an action is to be applied to the cell, controlling the means for controlling the displacement of the cell in order to immobilise the cell on the access zone and controlling the access zone in order to apply an action,
g) controlling the means of controlling the displacing of the cell in order to bring it to the outlet end.

In the case where the system for handling comprises second means for detecting between the access zone and the outlet end, a comparison of the signals emitted by the first means for detecting and the signals emitted by the second means for detecting can be carried out in order to detect a modification in at least one property of the cell following the action that has been applied to it.

The action can be a delivery of macromolecules, or the collection of one or several substances ejected by the cell, for example secretome.

By considering the deformability of the cell, the step d) can take a measurement of said deformability of the cell and makes it possible to deduce if it has a metastatic potential.

Preferably at least the steps e), f) and g) are controlled by a control unit.

BRIEF DESCRIPTION OF THE DRAWINGS

This invention will be understood better based on the following description and the accompanying drawings wherein.

DETAILED DISCLOSURE OF PARTICULAR EMBODIMENTS

In this application, the term "biological cells" means for example white blood cells having an approximate diameter between 7 µm and 18 µm, circulating tumour cells having an approximate diameter of about 10 ∞m, red blood cells having an approximate diameter between 6 µm and about 8 µm, bacteria having an approximate diameter of about 2 µm. The latter shall be designated in what follows as "cell".

The terms "upstream" and "downstream" are to be considered in the main direction of circulation of the cells in the system.

Figure 1:
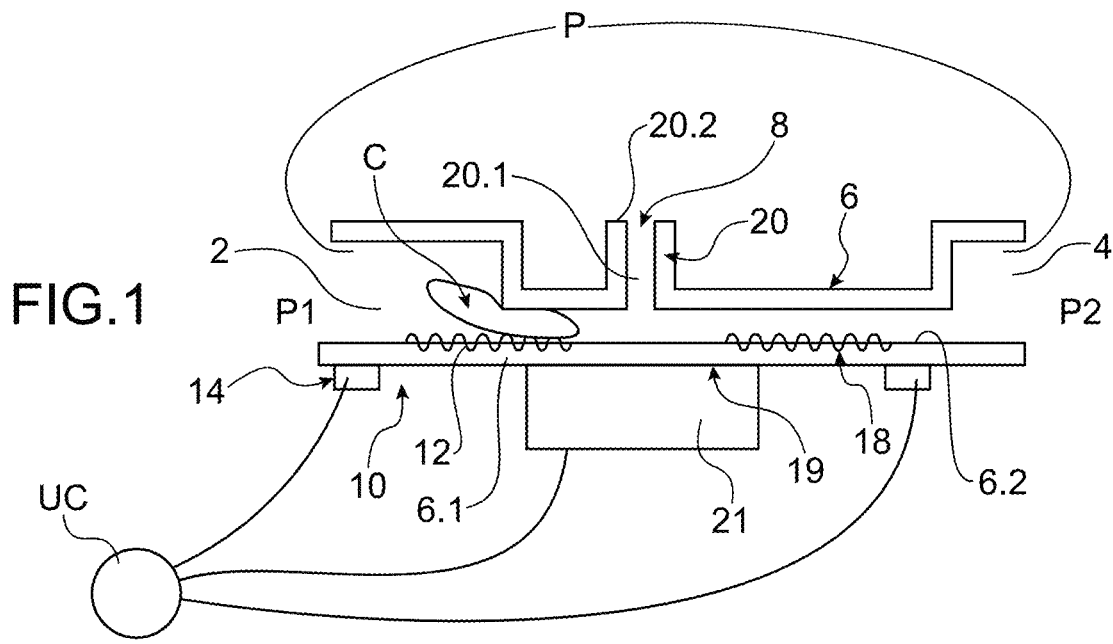
FIG. 1 is a diagrammatical longitudinal cross-section view of an embodiment of a microfluidic system for handling according to the invention.

FIG. 1 shows a diagrammatical cross-section view of a microfluidic system for handling biological cells. The biological cells are contained in a solution that allows them to live.

In this application, the term "handling a cell" means any action on a cell aiming for example to deliver to it for example macromolecules, to extract from the latter substances, forming secretome, but also Extracellular vesicles (EVs), among which exosomes, which could have been secreted by the cell secondarily following the application of a mechanical stress during the passing in the channel.

The system comprises a fluidic path that extends, upstream, from an inlet chamber 2 of the cells C intended to be handled to, downstream, an outlet chamber 4 of the biological cells having been treated.

The system comprises means P for circulating in order to circulate the cells between the inlet chamber 2 and the outlet chamber 4. In order to set the cells in motion, a first pressure P1 is applied in the upper inlet chamber at a second pressure P2 in the outlet chamber. The pressures P1 and P2 can be controlled as shall be seen in what follows. The means for circulating are for example a pump or any other means well known to those skilled in the art, such as a system for pressurising fluidic reservoirs containing the sample to be analysed, and for example biological buffers. The means can also make it possible to displace the cells from downstream to upstream, for example a reversible pump can be used, or by modifying the pressure differential applied between the microfluidic reservoirs arranged upstream and downstream.

The inlet chamber 2 is intended, for example, to be connected to a reservoir (not shown) containing the solution containing the cells to be handled and the outlet chamber 4 is intended to be connected to a reservoir (not shown) for collecting cells to be treated.

The inlet chamber 4 can contain several cellules C.

The system comprises at least one main channel 6 that connects the inlet chamber 2 and the outlet chamber 4. The main channel 6 has a transverse section less than the transverse section of the cells C to be handled in such a way that, when the cells are forced to circulate in the main channel 6, mechanical stresses are applied to them.

Advantageously, the main channel 6 has a diameter of about half of the characteristic dimension of the cell in suspension. For example it has a diameter between 5 μm and 10 μm according to the cellular type over a length for example between 10 μm and 40 μm.

The stresses applied to the cell slow down the displacement thereof in the system. By measuring the time taken by the cell to travel a certain portion of the main channel 6, it is possible to determine which cell it is. Indeed, the transit time of the cell depends on its physical properties, linked to its nature. Examples of techniques for measuring this time are described herein below.

The system comprises an access zone 8 from the outside opening into the main channel 6.

The system also comprises first means for detecting 10 the presence of a cell arranged at the inlet end 6.1 of the main channel 6 when a cell has engaged into the main channel 6. The means for detecting 10 are advantageously of the vibrating type. The first means for detecting 10 comprise a support 12 forming a portion of the wall of the main channel 6 and one or several actuators 14 able to set in vibration the surface 12. The actuators are advantageously piezoelectric actuators. Alternatively, this could be in a non-limiting way electrostatic, magnetic, thermal, etc. actuators.

The activation of the actuator or actuators generates a vibration wave in the support 12, this wave is modified by the presence of a cell, this modification in the wave is measured and supplies a piece of information on the presence of a cell. The vibrating support has a resonating frequency.

When the cell arrives, it bears against the vibrating support, which modifies its faculty to vibrate. This results in a modification of the resonance frequency. For example, by measuring the impedance of the system, it is possible to determine this modification in resonance frequency and therefore the modification of the vibration wave.

The vibrating support can be a plate able to generate Lamb waves or Rayleigh waves using actuators.

Figure 5:
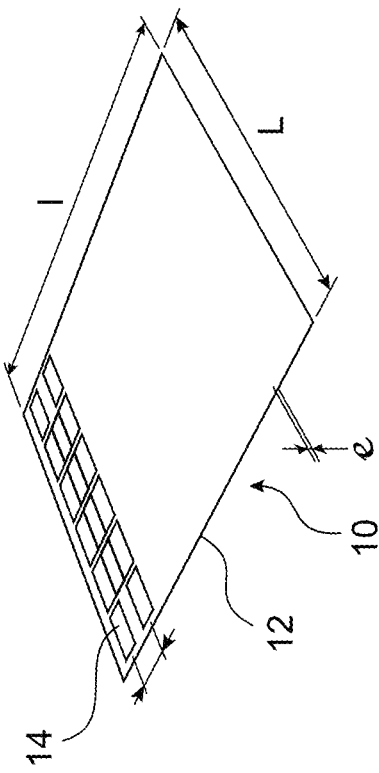
FIG. 5 is a diagrammatical perspective representation of an example of a vibrating support that can be implemented in the system according to the invention.

In FIG. 5, an example of a rectangular vibrating support can be seen provided with actuators 14 able to generate Lamb waves. For example the actuators 14 are distributed in rows in the width of the support and the rows are arranged next to one another in the direction of the length of the plated.

For example the support is made of glass, of which the width L is equal to 61 mm, the length l is equal to 82 mm and the thickness e is equal to 700 μm. Each actuator 14 has a length of 9 mm and a width of 5 mm and the actuators are separated from one another by 1 mm in the direction of the width of the support and the rows are separated from one another by 4 mm.

Advantageously, the vibrating support 12 is transparent.

Advantageously, second means for detecting 18 are provided downstream of the access zone. They are also advantageously of the vibrating type. They also make it possible to measure a modification in the wave due to the presence of a cell. By comparing the signals delivered by the first means for detecting 10 and the second means for detecting 18, it is possible to determine if the action carried out in the access zone 8 had an effect on the cell. It is also possible to deduce therefrom if the action has actually taken place.

The access zone 8, also called "window" opens into the side wall of the main channel 6 downstream of the means for detecting 10. This access zone makes it possible to access the cell that is circulating in the main channel 6 and to apply an action to it. This can be for example to transfect macromolecules in the cell and/or to sample one or several substances emitted by the cell.

In the example shown, the access zone comprises a channel 20 transversal to the main channel 6 and connected by an end 20.1 to the main channel 6. The other end 20.2 of the transverse channel 20 is intended to be connected to a secondary channel that can be connected for example either to a reservoir of macromolecules, or to a collection reservoir.

It can be considered that the section of the channel 6 varies, thus modifying the stresses applied to the cell. For example the section of the channel increases after the access zone.

Several assemblies in series can also be considered with each one comprising a channel with a reduced section and an access zone in order to carry out several actions successively. For example, a first assembly can be planned to recover the secretome of a cell in order to analyse it, then a second assembly intended to transfect the cell, for example according to the secretome recovered in the first assembly and a third assembly in order to recover the secretome after transfection.

Also advantageously, the wall 19 of the main channel 6 on the access zone is transparent in order to make it possible to produce images of the cell and/or to observe it. An imaging system 21 or imager can then be arranged outside the main channel 6 opposite the transparent wall. This is for example a camera or a CMOS imager.

This imaging system can make it possible to detect the cell when it is in the access zone. The transit time of the cell can be measured for example by following the path of the cell by the image given by the imager. By determining the time taken by the cell to travel the distance between the means for detecting and the imaging system, the cell can be identified. Such an identification then makes it possible to apply a suitable action.

The travel time of the cell can also be measured by following the resonance frequency of the vibrating surface. Indeed, the passage of the cell modifies the vibration frequency, thus the transit time of the cell in the channel restriction can be deduced from following the frequency.

Advantageously, the imager also makes it possible to obtain accurate images of the deformation of the cell once constrained in the channel. The deformation of the cell is also characteristic of the properties and therefore of the nature of the cell. It is then possible to correlate the transit time of the cell, i.e. when the cell crosses the fluidic restriction, measured for example using the variation in the resonance frequency of the vibrating support, with the morphological information obtained with the imager when the cell is deformed.

It could also be considered to use an additional imaging system downstream of the access zone in order to observe for example the effect of the action on the cells.

Very advantageously, the system comprises a control unit UC connected to the first means for detecting, optionally to the second means for detecting, and to the imaging system. Furthermore the control unit is able to control the action to be applied to the cell. Thus the action can be triggered automatically and in a synchronised manner according to the signals emitted by the means for detecting and the imaging system.

The general operation of the system for handling of FIG. 1 shall now be described.

One or several cells are put into suspension in the inlet chamber.

The pump is activated in order to convey the cell to the inlet 6.1 of the main channel and to displace the cell in the main channel 6.

In light of the section of the main channel 6, a single cell can enter at a time in the main channel 6.

When the cell has arrived at the inlet of the main channel 6, it comes into contact with the vibrating support of the first means for detecting 10. The vibrating support has a vibration mode, such as for example a surface wave, such as the Rayleigh or Lamb waves.

The surface wave is modified by the presence of the cell. Indeed the cell induces a variation in the stiffness or mass of the vibrating support the frequency is then offset because the frequency is proportional to V(k/m).

The presence of a cell at the inlet of the main channel is therefore detected by this modification in the surface wave.

Furthermore, using the variations of the properties of the vibrating surface, the mechanical properties of the cell can be deduced, such as the mass, elasticity. The density can also be deduced from these variations by knowing the density of the solution.

Very advantageously, due to the reduced section of the main channel 6, the cell is deformed by being displaced in the latter, which makes it possible to optimise the measuring of the deformability of the cell via the image of the deformed cell given by the imager. This information makes it possible to deduce the metastatic potential in the case of Circulating Tumour Cells.

The vibrating support furthermore offers assistance to the displacement of the cell in the main channel 6.

The presence of a cell is detected and thus cell is identified or at least one portion of its properties is determined.

The treatment unit can then generate orders in order to apply an action on the cell on the access zone. This action can be, for example, either a transfection, or a collection of substances ejected by the cell.

On the one hand the system is more effective because it acts when a cell is present and it is capable of applying an action adapted to the cell according to its properties.

When the cell has been subjected or not to an action on the access zone, it continues its displacement in the direction of the outlet chamber. It then comes into contact with the second means for detecting. The modifications of the surface wave also make it possible to obtain information on the properties of the cell. By comparing these properties with those determined with the information provided by the first means for detecting, it is possible to determine if the action took place and/or had an effect on the cell.

For example if it is detected that the action did not have any effect, it can be decided to send the cell back to the access zone in order to have it again be subjected to the action, by inverting the direction of displacement imposed by the microfluidic pumping or pressurisation system. Alternatively, the cell can be conveyed to a second access zone downstream of the access zone 8 in order to apply a new action to it. It can be considered as an alternative to send the cell back to the access zone in order to have another action applied to it.

The cellule is displaced to the outlet chamber in order to be collected or removed.

Thanks to the invention, the entire process that the cell is subjected to can be automated.

Figure 2:
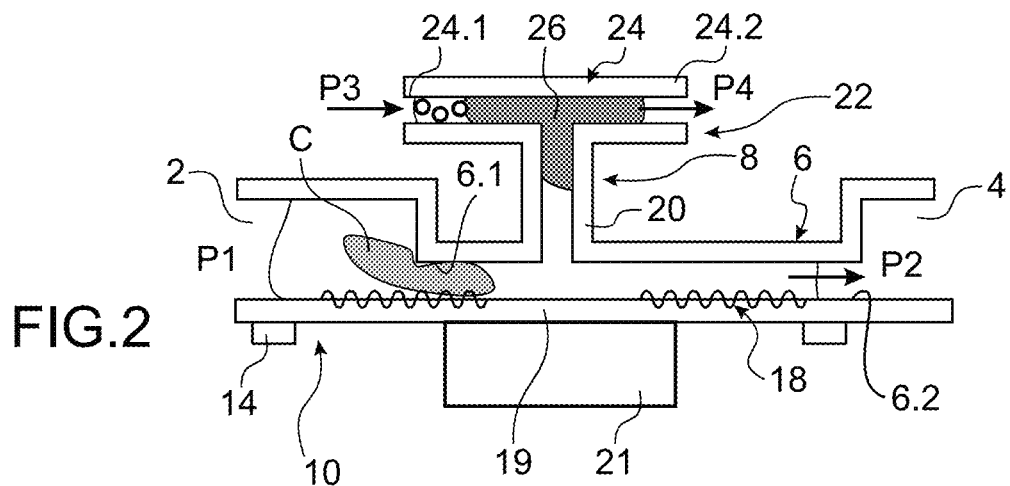
FIG. 2 is a diagrammatical longitudinal cross-section view of an embodiment of a microfluidic system for handling according to the invention comprising means for delivering macromolecules.

FIG. 2 shows an example of a system adapted to the transfection.

In this example, the transverse channel 20 of the access zone comprises on its end 20.2 means for connecting to the reservoir of macromolecules.

The means for connecting 22 comprise a secondary channel 24 provided with a first end 24.1 and with a second end 24.2. The end 20.2 of the transverse channel 20 opens into the side wall of the secondary channel 24 between its first end 24.1 and its second end 24.2. The first end 24.1 is intended to be connected to a reservoir of macromolecules or any other substance to be transfected.

The first end 24.1 is subjected to a third pressure P3 and the second end 24.2 is subjected to a fourth pressure P4.

Furthermore a means for closing 26 is arranged between the ends 20.2, 24.1 and 24.2 in such a way as to isolate the ends 20.1, 24.1 and 24.2 from one another. The means for closing is for example formed by the oil or any other liquid material immiscible with the solutions containing the cells and the macromolecules.

Alternatively, any other means for connecting, of the hydraulic valve type, could be implemented.

The proceedings of the transfection is as follows:

Initially the pressures P3, P4 and the pressure in the transverse channel 20 are such that the means for closing 26 isolates the solution containing the macromolecules from the transverse channel 20 and from the main channel 6.

On the one hand, thanks to the signal transmitted by the means for detecting 10, the control unit is informed of the presence of a cell at the inlet of the main channel 6. The control unit can then trigger the transfection. The system according to the invention therefore allows for a synchronisation between the detecting and the triggering of the action.

For this the cell C is immobilised on the access zone in such a way as to be opposite the end 20.1 of the transverse channel 20. For example the pressures P1 and P2 are rendered equal or the pressure P1 is sufficiently lowered so that the cell is immobilised and closes the first end 20.1 of the transverse channel 20.

Then, the pressures P3 and P4 are controlled do that the means for closing 26 is displaced to the second end 24.2 and places into communication the first end 24.1 and the transverse channel 20. Furthermore, the pressure P3 is controlled in such a way as to be greater than that in the transverse channel 20 causing a flowing of the solution containing the macromolecules to the transverse channel 20. The macromolecules come into contact with the portion of the membrane of the cell that closes the end 20.1. Furthermore due to the mechanical constraints applied to the cell by the reduced section of the main channel 6, pores advantageously temporary are formed in the membrane allowing for the delivery of macromolecules in the cell.

When the delivery is completed, the pressures P3 and P4 are modified in such a way as to put the closing element 26 back into the initial position isolating the transverse tube 20 from the first end 24.1 and the cell is again displaced in the direction of the outlet chamber 4. The pores, when they are temporary, close up when the cell exits from the main channel 6.

It can be provided to subject the cell to various stimuli such as cytokines, molecules that facilitate the secretion of exosomes such as calcium ionophore.

Another action that can be carried out on the access zone is the collecting of substances emitted by the cell subjected to the mechanical constraints applied by the channel with a reduced section 6.

The cell ejects substances that are found in the secondary channel 20. By controlling the pressures P1, P2, P3 and P4 the substances can be collected on the first end 24.1 or the second end 24.2 of the secondary channel 24.

The substance or substances ejected by the cell, due to the constraint that was applied to it by forcing it to pass in the main channel 6, can be secretome, comprising in particular Extracellular vesicles (EVs) (among which the exosomes described in Sheridan C. *Exosome cancer diagnostic reaches market Nat Biotechnol.* 2016 April; 34(4):359-60.]

These substances can be analysed and/or collected.

In an advantageous example, it is possible to associate with the access zone means for analysing substances ejected by the cell and recovered. For example, the means for analysing can be mass spectrometer (MALDI-TOF-MS/MS: Matrix-assisted laser desorption/ionization-Time of Flight-Mass spectrometry), a fluorescent marker, a device for analysing via the chain reaction by polymerase or PCR (Polymerase Chain Reaction), proteomics, a device for counting and weighing EVs via a resonator suspended from a nanochannel or SNR(Suspended Nanochannel Resonator), a passive microfluidic device of the deterministic lateral displacement type or DLD (Deterministic Lateral Displacement) in order to isolate by size range subpopulations of extracellular vesicles (of which the size varies between 30 nm and 1 μm), RAMAN (among these methods that based on Raman spectroscopy, amplified by the surface or SERS (Surface Enhanced Raman Spectroscopy), flow cytometry, dynamic scattering of the light or DLS (Diffusion Light Scattering).

In the case of adherent cells, the latter secrete proteins from the extracellular matrix, of which the structural and functional study is very important in the analysis of cells.

Moreover, due to the reduced section of the main channel 6, the cell is constrained at the inlet of the channel. The deformability of the cells associated with the reduction in the section of the channel can advantageously be a characterisation element of the state of the cell. It is advantageously possible to analyse this deformability, for example by optical microscopy, for example in order to measure the time of passage in a constricting channel.

Thanks to the system of the invention, it is possible to consider studying the effect of a mechanical constraint applied to the cell by the main channel 6, on the modification of the secretion of exosomes of a cell chemically stimulated or not, by implementing methods for collecting and methods for analysing these exosomes in the access zone such as has been described hereinabove.

Figure 3:
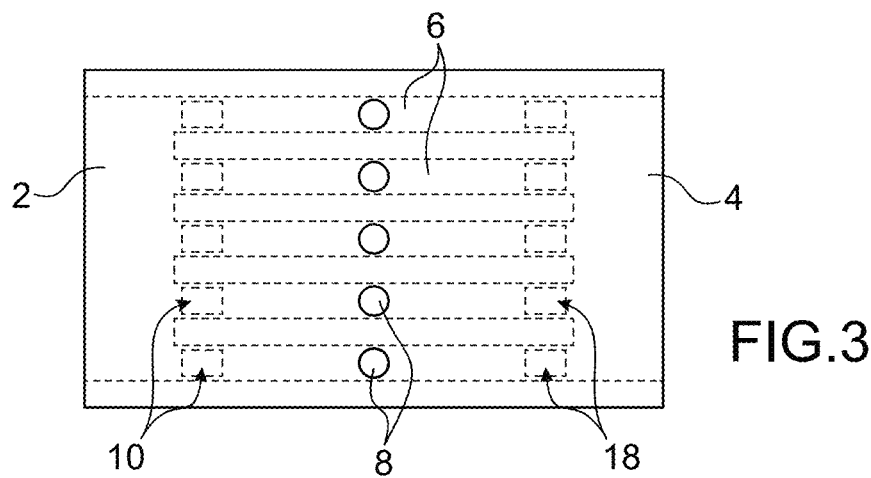
FIG. 3 is a top diagrammatical view of an example of a microfluidic system for handling that allows for a simultaneous treatment of several cells.

FIG. 3 shows a diagrammatical top view of a microfluidic system according to the invention comprising several parallel channels 6 connected to the inlet chamber and to the outlet chamber. The channels are supplied in parallel and it is possible to apply the same action or different actions to several cells simultaneously.

Alternatively, each channel could have its own inlet chamber separated from the other inlet chambers and/or its own outlet chamber separated from the other outlet chambers.

The channels can have the same section and be used for example to handle the same cells or the same type of cell, or they can have different sections and handle cells of different sizes.

All or a portion of the channels can share the same access zone, with then the same action being applied to all or a portion of the cells. However each channel has its own access zone, which allows for a different action for each channel.

The implementing of several channels makes it possible to have a redundancy in the information obtained on the cells, to increase the analysis flow rate, the treatment flow rate, the collection flow rate, etc.

As an example, the system could comprise 10 channels in parallel, with each channel being individually controlled by a means for microfluidic regulation, such as a pump or a system for pressurising reservoirs.

An example of the method for carrying out the system for handling cells according to the invention shall now be described using FIGS. 4A to 4Q.

The device will be for example made of glass, but other materials can be used for example PDMS.

Figure 4A:
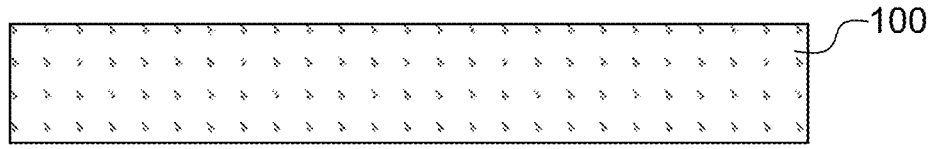
FIGS. 4A to 4Q are diagrammatical representations of different steps of an example of a method for producing a microfluidic system for handling according to the invention.

A substrate made of glass 100 is shown in FIG. 4A

Figure 4B:
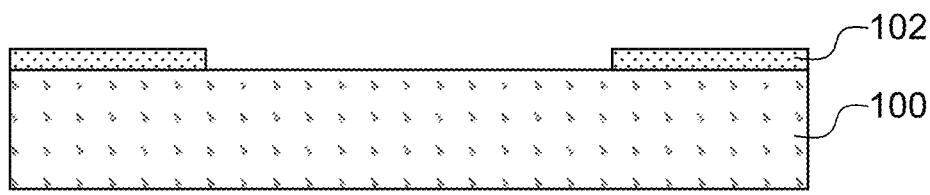

During a first step, a mask is formed by lithography 102 on the front face of the substrate 100 (FIG. 4B), in such a way as to create a first cavity 104 on the front face by etching. The mask is then removed.

Figure 4C:
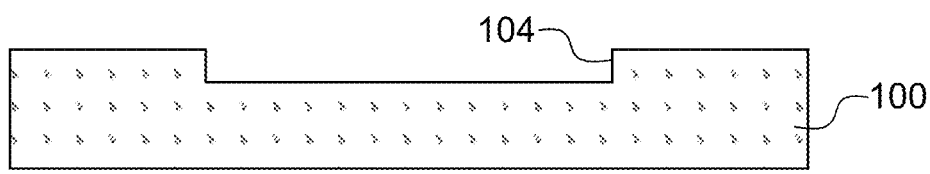

The element thus obtained is shown in FIG. 4C.

During a following step another mask 106 is deposited in order to structure the cavity 104.

Figure 4D:
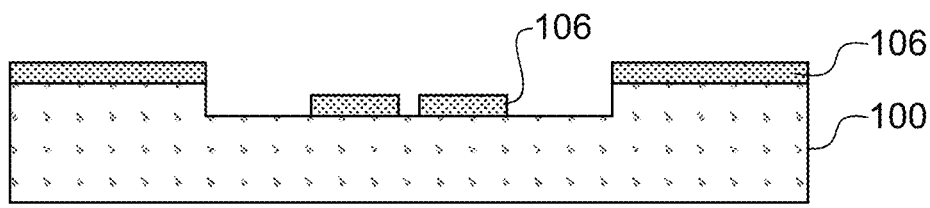

The element thus obtained is shown in FIG. 4D.

During a following step, the bottom of the cavity is structured in such a way as to form three other cavities 108, 110, 112, for example by etching.

Figure 4E:
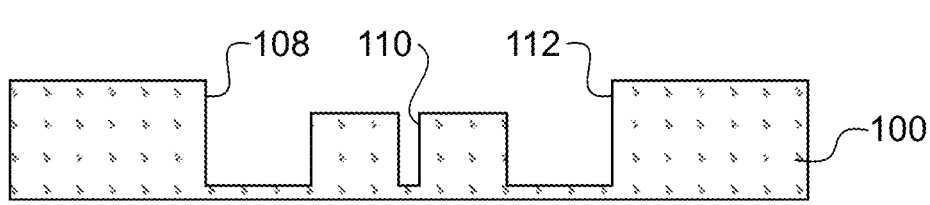

The element thus obtained is shown in FIG. 4E.

During a following step, the bottom of the cavities 108, 110 and 112 is structured, for example by etching, in such a way that they open at the rear face of the substrate 100.

Figure 4F:
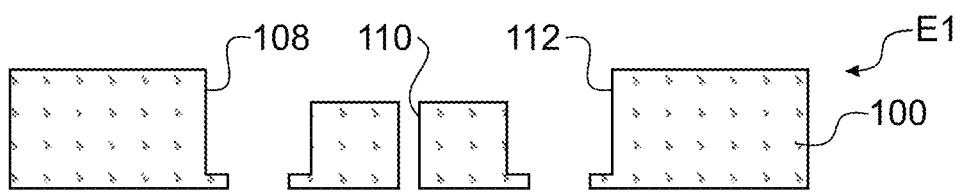

The element E1 thus obtained is shown in FIG. 4F.

Figure 4G:
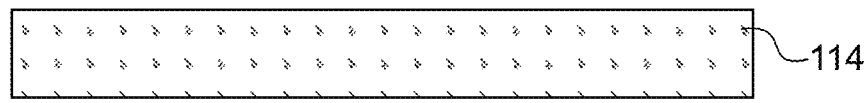

Another substrate 114 is then used, for example also made of glass (FIG. 4G).

Figure 4H:
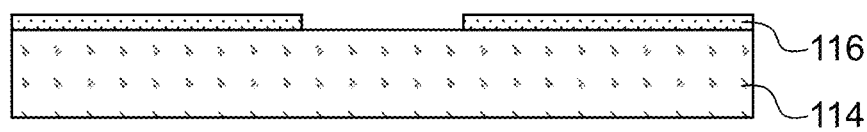

During a following step, a mask 116 is formed on the front face of the substrate 114 (FIG. 4H), in such a way as to create a first cavity 118 on the front face by etching. The mask is then removed.

Figure 4I:
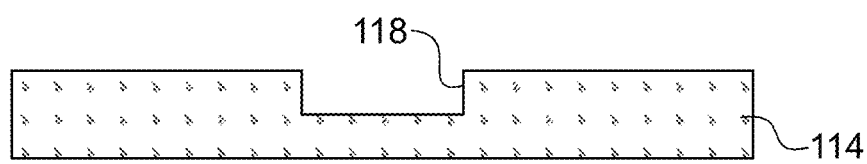

The element thus obtained is shown in FIG. 4I.

During a following step, another mask 120 is formed on the front face of the substrate 114 and on a portion of the bottom of the cavity 118.

During a following step, the substrate is structured in such a way as to form four cavities 122, 124, 126, 128 that open into the rear face of the substrate 114. The cavities 122 and 128 are located on either side of the 118 and the cavities 124, 126 are located in the cavity 118.

Figure 4J:
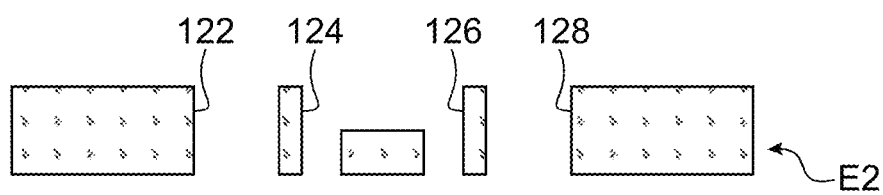

The element E2 thus obtained is shown in FIG. 4J.

During a following step, the elements E1 and E2 are assembled, the front face of the element E2 being in contact with the rear face of the element E1 and in such a way that the cavities 108 and 112 open into the cavities 122 and 128 and the cavity 110 opens into the cavity 118. The assembly is for example carried out by anode sealing or molecular sealing. An element E3 that can be seen in FIG. 4Q is obtained.

A support is moreover carried out intended to close the channel 6 and comprising the first means for detecting 10, and the second means for detecting and a transparent zone for an imaging system.

In the description that follows, only the carrying out of the first means for detecting is described, but the carrying out of the second means for detecting can be simultaneous to that of the first means, and the second means for detecting have a structure close to that of the first means.

Figure 4K:
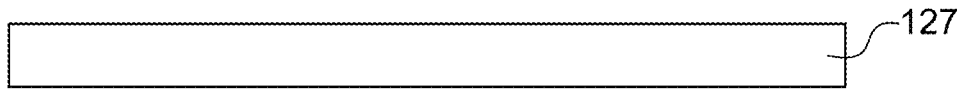

Another substrate 127 is used, for example made of glass (FIG. 4K).

The piezoelectric actuators are carried out by:
formation of a layer 130 intended to form one of the electrodes, for example made of Mo on the front face of the substrate 127, for example by full plate deposition,
formation of a layer 132 of piezoelectric material for example PZT, AlN, ZnO, etc., for example by full plate deposition, and
formation of another layer 134 intended to form the other electrode, for example made of MO, for example by full plate deposition.

Advantageously a layer 129 intended to orient the material of the electrode layer 130 for the purpose of orienting the piezoelectric material is formed prior to the deposition of the layer 130. For example the layer 129 is a thin layer of AlN whereon is deposited the Mo, then the AlN.

Figure 4L:
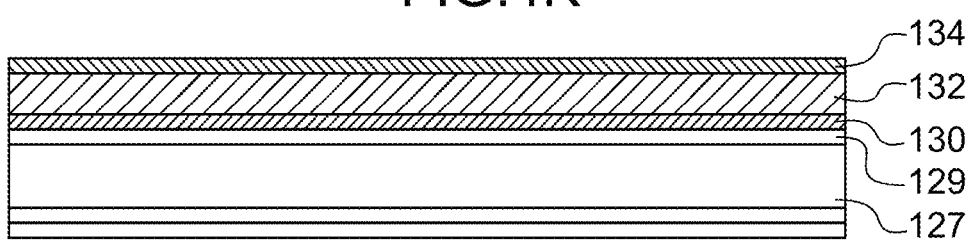

The element thus obtained is shown in FIG. 4L.

During a following step, the layers 130, 132 and 134 are structured successively, for example by etching.

Figure 4M:
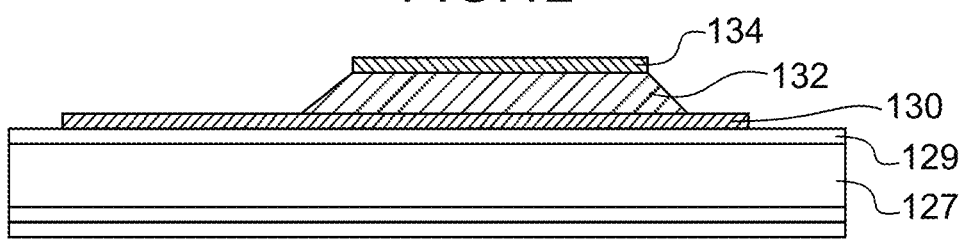

The element thus obtained is shown in FIG. 4M.

Figure 4N:
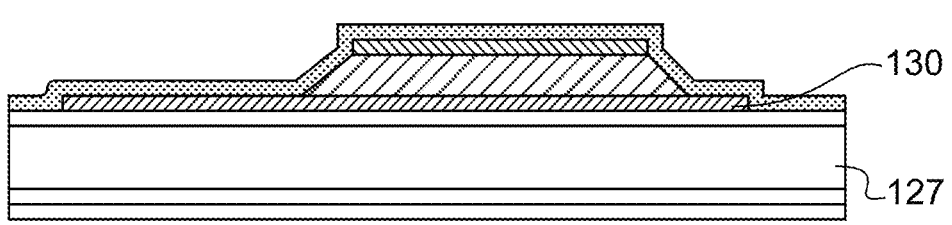

During a following step, a passivation layer 136 is formed on the front face of the element of FIG. 4N, for example a layer of oxide, for example of a thickness 300 nm. For example the passivation layer is oxide $SiO_2$ deposited via PECVD (plasma enhanced chemical vapour deposition).

The element thus obtained is shown in FIG. 4N.

During a following step, the layer 136 is structured, for example via photolithography and etching, to open the layer 136 on electrodes and allow for the carrying out of contact.

Figure 4O:
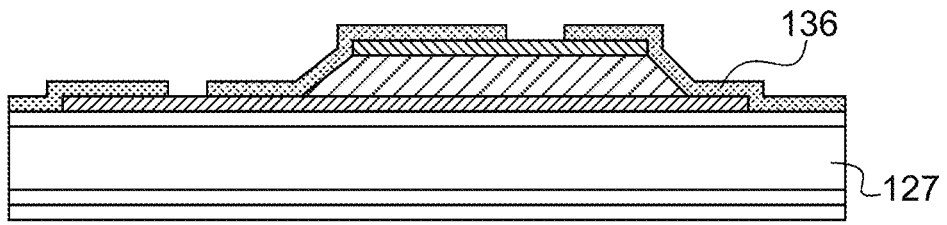

The element thus obtained is shown in FIG. 4O.

During a following step, an electric conductive layer 138, for example made of gold, is formed on the oxide layer and comes into contact with the electrodes on openings in the layer 136.

Figure 4P:
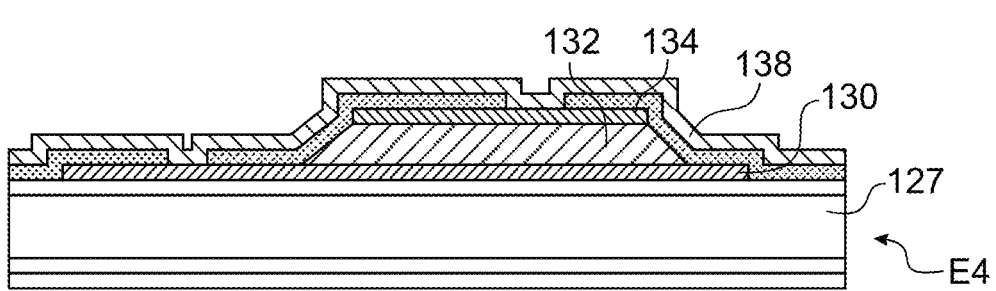
Figure 4Q:
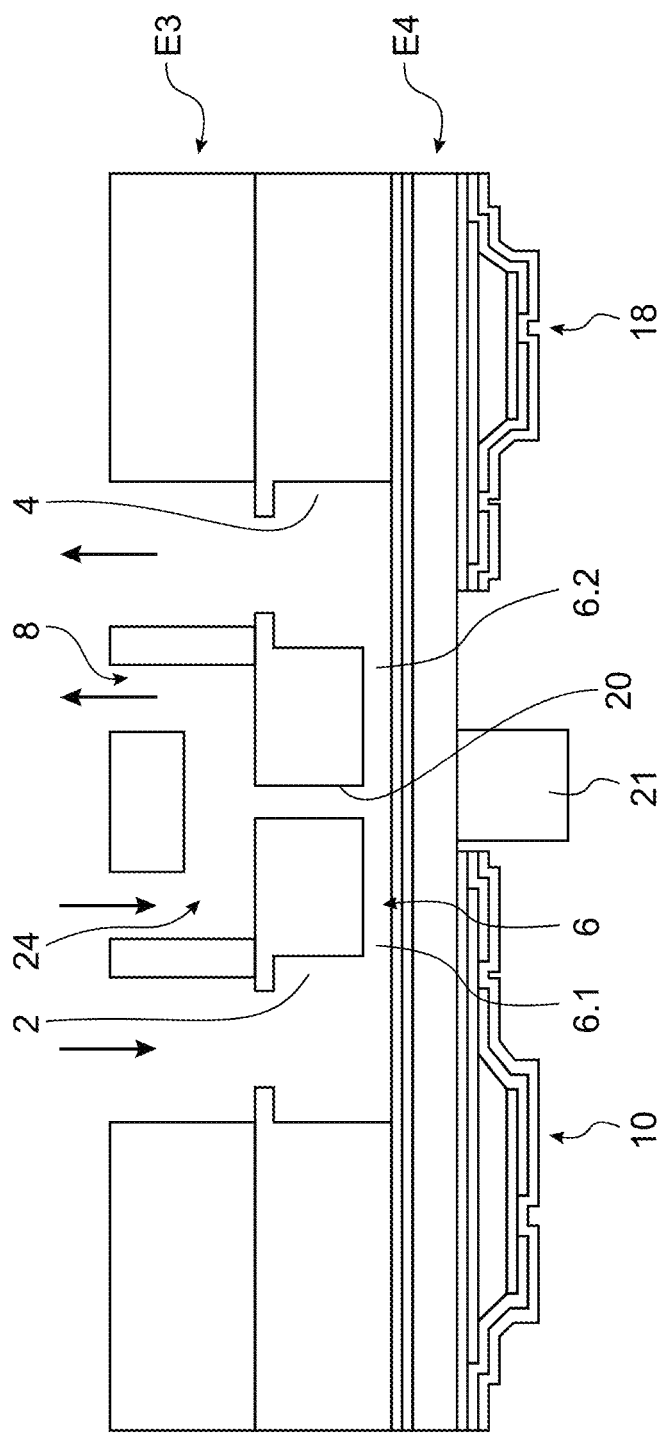

The element E4 thus obtained is shown in FIG. 4P.

The element E4 is then assembled with the element E3 in such a way that the rear faces of the two elements are in contact. The elements E3 and E4 are assembled for example by depositing an adhesive by screen printing process in such a way as to be located solely on adhesive zones or the by anode gluing of the two faces of glass of the elements E3 and E4.

The system for handling according to the invention (FIG. 4Q) is then obtained.

In this example the actuators are outside the channel but it could be provided that they be inside the channel.

In the example shown the zone between the two actuators allows for the setting up of an imaging device, for example of the CMOS type.

The invention claimed is:

1. A handling system for handling biological cells, comprising:
n main channels, n being a whole number at least equal to 1, with each main channel comprising an inlet end, an outlet end, and at least on a first portion starting from the inlet end;
at least a first detector configured to detect presence of a cell on the inlet end of said each main channel;
at least one access zone opening into the main channel between the inlet end and the outlet end in said first portion, in order to exert an action on said detected cell; and
a device configured to displace said detected cell for controlling the displacement of the detected cell between the inlet end and the outlet end, said device being configured in such way that the detected cell enters into the main channel by the inlet end and exits from the main channel by the outlet end, wherein
said each main channel further comprises a transverse section that is smaller than a transverse section of the detected cell, such that the detected cell circulating in said first portion undergoes mechanical stresses applied by the first portion,
the at least said first detector comprises a support forming a portion of a wall of the main channel, and
at least one actuator is configured to put said support into vibration, wherein
the access zone comprises a secondary channel and a device configured to interrupt a fluidic communication between the secondary channel and the main channel,
the device configured to interrupt a fluidic communication between the secondary channel and the main channel comprises a closing element, which is configured to be subjected in the secondary channel to two pressures being exerted in opposite directions, said device configured to interrupt a fluidic communication between the secondary channel and the main channel controlling said pressures in order to displace the closing element, and
the closing element is a fluid that is immiscible with at least a liquid that contains the detected cell.

2. The handling system according to claim 1, wherein the at least said first detector is configured to provide information on at least one property of the detected cell.

3. The handling system according to claim 1, further comprising at least a second detector between the access zone and the outlet end.

4. The handling system according to claim 1, wherein the secondary channel is configured to be supplied with one or several substances to be delivered to the detected cell.

5. The handling system according to claim 1, wherein the secondary channel is configured to be connected to a zone for collecting one or several substances ejected by the detected cell.

6. The handling system according to claim 5, wherein the secondary channel is configured to be connected to an analyzer configured to analyze the substance or substances ejected by the detected cell.

7. The handling system according to claim 1, wherein
at least one portion of a side wall of the main channel is transparent, and
the handling system further comprises an imaging system arranged on a transparent portion.

8. The handling system according to claim 1, further comprising control circuitry connected at least to the at least said first detector, to the access zone, and to the device configured to displace said detected cell, said control circuitry being configured to act at least on the access zone and/or on the device configured to displace said detected cell in order to apply an action to the detected cell.

9. The handling system according to claim 1, wherein n is equal to at least two.

10. The handling system according to claim 1, wherein
the at least said first detector comprises a support forming a portion of a wall of the main channel, and
said at least one actuator is a piezoelectric actuator.

11. The handling system according to claim 1, wherein the detected cell undergoes the mechanical stresses while passing through the main channel.

12. The handling system according to claim 1, wherein the mechanical stresses are modified by a section of the main channel.

13. A method for implementing a handling system for handling biological cells, the handling system comprising: n main channels, n being a whole number at least equal to 1, with each main channel comprising an inlet end, an outlet end, and at least on a first portion starting from the inlet end, a transverse section of said each main channel such that a cell circulating in said first portion undergoes mechanical stresses, the transverse section of the main channel being smaller than a transverse section of the cell; at least a first detector configured to detect presence of said cell on the inlet end of said each main channel; at least one access zone opening into the main channel between the inlet end and the outlet end in said first portion, in order to exert an action on said cell; and a device configured to displace said cell for controlling the displacement of the cell between the inlet end and the outlet end, said device being configured in such way that the cell enters into the main channel by the inlet end and exits from the main channel by the outlet end, the method comprising:
- supplying of a solution that contains at least one cell at the inlet end of the main channel;
- displacing of the cell in the main channel;
- detecting of the presence of the cell at the inlet of the main channel;
- determining of at least one property of the cell and optionally the determining of said cell;
- deciding whether to apply an action to the cell;
    - if an action is to be applied to the cell, controlling the device configured to displace said cell in order to immobilize the cell at the access zone and controlling the access zone in order to apply an action; and
- controlling the device configured to displace said cell in order to bring the cell to the outlet end, wherein
- the handling system comprising at least a second detector between the access zone and the outlet end, and
- a comparison of signals emitted by the at least said first detector and signals emitted by the at least said second detector is carried out in order to detect a modification in at least one property of the cell following the action that has been applied to the cell.

14. The method for handling according to claim 13, wherein the action is a delivery of macromolecules.

15. The method for handling according to claim 13, wherein said at least one property of the cell being a deformability, the determining takes a measurement of said deformability of the cell and determines whether the cell has a metastatic potential.

16. The method for handling according to claim 13, wherein at least the deciding, controlling the device configured to displace said cell in order to immobilize the cell, and controlling the device configured to displace said cell in order to bring the cell to the outlet end are controlled by control circuitry.

17. The method for handling according to claim 13, wherein the action is collection of one or several substances ejected by the cell, including secretome.

* * * * *